United States Patent [19]

Barfknecht et al.

[11] Patent Number: 4,629,738

[45] Date of Patent: Dec. 16, 1986

[54] NON-CLASSICAL TOPICAL TREATMENT FOR GLAUCOMA

[75] Inventors: Charles F. Barfknecht; Ronald D. Schoenwald, both of Iowa City, Iowa

[73] Assignee: University of Iowa Research Foundation, Iowa City, Iowa

[21] Appl. No.: 624,261

[22] Filed: Jun. 25, 1984

[51] Int. Cl.$^4$ .............................................. A61K 31/18
[52] U.S. Cl. ..................................... 514/603; 514/604; 514/913
[58] Field of Search ................ 514/603, 604; 548/136, 548/139, 165; 564/83

[56] References Cited

U.S. PATENT DOCUMENTS 3,726,892  4/1973  Cebalo ................................ 548/139
4,132,786  1/1979  Moreau et al. ....................... 564/83
4,305,927  12/1981  Theeuwes et al. .................... 424/80

FOREIGN PATENT DOCUMENTS 508982   1/1955   Canada ................................ 548/139
003635   9/1981   European Pat. Off. .
1338945  11/1963  France ................................ 564/83
43-4253  2/1965   Japan .................................. 564/83
858786   1/1961   United Kingdom .................... 564/83

OTHER PUBLICATIONS

Gelatt et al.—Am. J. Vet. Res. 40(3)—334–345 (1979).
AMA Drug Evaluation—2nd ed. (1973)—pp. 676, 678, 679 and 684–685.

Primary Examiner—Douglas W. Robinson
Attorney, Agent, or Firm—Zarley, McKee, Thomte, Voorhees & Sease

[57] ABSTRACT

A topical composition for eye treatment of glaucoma, comprising a small but pharmaceutically effective amount of a non-classical carbonic anhydrase inhibitor. The most preferred compound is methyl acetazolamide. The invention also relates to a method of topically treating glaucoma with eye drops of a non-classical carbonic anhydrase inhibitor to reduce intraocular pressure.

8 Claims, No Drawings

NON-CLASSICAL TOPICAL TREATMENT FOR GLAUCOMA

GRANT REFERENCE

This invention was made with government support under Contract No. 5 RO1 EY 03297-02 awarded by the National Eye Institute. The government has certain rights in this invention.

CROSS REFERENCE TO A RELATED APPLICATION

This application is a continuation-in-part of Ser. No. 464,061, filed Feb. 4, 1983, now U.S. Pat. No. 4,483,864, and is also a division of Ser. No. 512,234, filed July 11, 1983, now U.S. Pat. No. 4,483,872.

BACKGROUND OF THE INVENTION

Glaucoma, which some estimate affects 2 million adults over 40, is an impairment of vision caused by too much fluid pressure within the eye.

Surgical treatment for glaucoma does not represent a long term cure. While it is effective, it is also expensive and traumatic, and some surgeons will use surgery only as a last resort.

Carbonic anhydrase inhibitors, prescribed orally work well to treat this disease, but they carry a host of side effects, from nausea to kidney stones. The preferred method of treatment for the disease is instillation by drops to the eye; however, carbonic anhdrase inhibitors have not proven effective when given this way.

Glaucoma stems from an excess of fluid behind the cornea, the three-layered tissue that acts as a window to let light enter. Fluid carrying nutrients such as potassium and glucose constantly wash the inside of the cornea to keep it healthy, much as tears wash the outside of the cornea.

In some middle-aged adults, fluids build up faster than can be absorbed back into the blood, for one of two reasons: the ciliary body (a tiny tissue behind the iris) may excrete too much fluid, or the fluid may not drain off at the normal rate.

Either way, the excess fluid damages the optic nerve. At first, a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral—each have a peculiar set of side effects.

To make the long journey, oral drugs must be dosed in very high concentration. One class of drugs, called carbonic anhydrase inhibitors when taken orally slow the formation of fluid by inhibiting a chemical reaction at the ciliary body. Along with their well-tested effectiveness, comes nausea, tingling in fingers and toes and other side effects. Oral drugs generally do not, however, cause side effects in the eye.

Certain topical drugs, other than carbonic anhaydrase inhibitors, e.g., pilocarpine, while causing less systemic effects, can cause severe headaches and constrict the pupil, making the daytime appear dark.

Accordingly, there is a real and continuing need to develop an inhibitor drug that can be dropped into the eye instead of shallowed, thereby avoiding the present side effects.

It is a primary objective of the present invention to develop a highly effective topical carbonic anhydrase inhibitor drug (which previously is only effective orally) for treatment of glaucoma to reduce intraocular eye pressure, and at the same time, avoid the systemic side effects, commonly caused by oral drugs.

Another objective of the present invention is to develop a drug for topical treatment of glaucoma, which is not only effective, but which will also pass through the three layered cornea and still be effective enough to work on the ciliary body.

Another objective of the present invention is to develop a highly effective, topical drug treatment for glaucoma which is substantially non-harmful to the eye when topically applied.

An even further objective of the present invention is to develop an eye treating topical composition which is effective for glaucoma treatment.

A still further objective is to provide a convenient method of synthesis of certain new and novel compounds which are highly effective topical treatments for glaucoma.

A further specific objective of the present invention is to provide as a novel compound, N-methyl-2-acetylamino-1,3,4-thiadiazole-5-sulfonamide (methyl acetazolamide), which in pharmaceutically effective amounts is a highly effective topical composition for eye drop treatment of glaucoma.

The method and manner of achieving each of the above objectives, as well as others, will become apparent from the detailed description of the invention which follows hereinafter.

SUMMARY OF THE INVENTION

A topical composition for eye drop treatment of glaucoma wich comprises a small but phamaceutically effective amount of N-alkylated sulfonamides of carbonic anhydrase inhibitors of the formula:

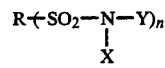

with the constituents as hereinafter defined.

The invention also relates to the most highly preferred compound methyl acetazolamide, which is a compound falling into the general formula presented above. The invention further relates to a method of topically treating glaucoma with eye drops to reduce intraocular eye pressure.

DETAILED DESCRIPTION OF THE INVENTION

As heretofore mentioned, carbonic anhydrase inhibitors are known. However, the compounds are generally not effective because of the rather severe side effects previously mentioned. Studies have shown that when taken orally, because of the side effects, approximately 80% of the treated patients stop taking the drug treatment within two to three weeks. The side effects that they often report are short-term tingling of the extremities, gastrointestinal tract upset, kidney stones and some renal failure.

The mechanism of reaction of carbonic anhydrase inhibitors has been reported, and it involves a reduction of intraocular pressure in the eye. The compounds useful for treatment in this invention function to provide reduction of intraocular pressure, but do so without the commonly occurring side effects of oral drugs for treating glaucoma, or the commonly occurring side effects of topical drugs for glaucoma treatment.

The compounds developed by the applicants and useful for the topical composition eye drop treatment of glaucoma, as described in this invention are N-alkylated, N-alkylated-N-hydroxylated, and N-hydroxylated carbonic anhydrase inhibitors. They have the following general formula:

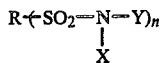

wherein
- R is selected from the group of substituted benzothiazoles, 2-acylamino-1,3,4-thiadiazole-5-, 2-acylamino-2-methyl-1,3,4-thiadiazole-5-, and dichlorophenyl-1,3-disulfonamide; and
- "X" is selected from the group of hydrogen, and hydroxyl, and
- "Y" is selected from the group of $C_1$ to $C_6$ alkyl and hydrogen and if either "X" or "Y" is hydrogen, the other is not hydrogen; and
- "n" is a whole number integer and is 1 or 2.

In certain other compounds of this invention, R can also be selected from aryl (preferably phenyl) or substituted aryl groups with substitutions on the phenyl group, particularly at 4 position, being for example chloro, nitro, fluoro, hydroxy, hydroxyethoxy, methoxy and ethoxy. it is also possible that either the 2 or 3 position may be substituted, with like groups, and that multiple substitutions such as 2,4-difluoro, 4-chloro-2-hydroxy, etc. may exhibit activity.

Of course, the compound is carried in an inert, non-eye irritating, non-toxic eye drop diluent of conventional formulation. Such formulations are well known, and commonly referred to in, for example, the *Physician's Desk Reference for Ophthalmology* (1982 Edition, published by Medical Economics Company, Inc., Oridell, N.J.), wherein numerous sterile ophthalmologic ocular solutions are reported, e.g., see pp. 112–114, which are incorporated by reference.

Preferably the amount of the N-substituted carbonic anhydrase inhibitors present in the eye drop treatment composition is a concentration of from about 0.25% to about 5% by weight of the eye drop treating composition. Most preferably, the amount is from about 0.5% to about 2.0% by weight of the eye drop treating composition, and in tests conducted to date, highly effective compositions have used the compounds at the 1% suspension level.

As heretofore mentioned, while the diluent is not part of the present invention in that such diluents are known, it is preferred tha the diluent be an isotonic eye treatment carrier, buffered to a pH within the range of from about 4.0 to about 8.0 and containing a small but effective amount of a wetting agent and an anti-bacterial agent. The preferred pH range is from about 6.8 to about 7.8.

Commonly used wetting agents are well known, and again are mentioned in the previously referred to pages of the *Physician's Desk Reference for Ophthalmology*. One suitable one is Tween, and in particular, Tween 80. Likewise, anti-bacterials are known and commonly employed in such compositions. Suitable anti-bacterials include the most preferred benzalkonium chloride and others as well such as, for example, chlorobutanol. The amount of wetting agent can range from 0.01% to 0.10%.

The amount of anti-bacterial can range from about 0.004% to about 0.02% by weight of the eye drop treating composition.

The compounds of this invention, providing that the molecular structures are as defined hereinbefore, have water solubility, but they also have a lipid solubility factor to allow transfer across the eye, and they have suitable structure to allow them to effectively function in the eye as carbonic anhydrase inhibitors. Their water solubility means ease of preparation for topical application, their lipid solubility characteristics mean effectiveness in transfer across the three corneal layers and into the target site (ciliary body).

The compound which is most preferred, because of its effectiveness and has been so far demonstrated to be the best of the non-classical type, is methyl acetazolamide, which with reference to the previously provided formula: R=(2-acetylamino-1,3,4-thiadiazole-5-]N-methylsulfonamide; "X" is hydrogen; "Y" is methyl and "n" is one. This is surprising. Within the classical thought it is well known that a free sulfonamide, unsubstituted on the nitrogen, is necessary for inhibition of carbonic anhydrase, both in vitro and in vivo see R. O. Roblin, Jr., et al, "Journal of the American Chemical Soc.", Vol. 72, p. 4890 (1950). Surprisingly, methyl acetazolamide, where the nitrogen is substituted, is able to reduce intraocular pressure (IOP) after topical administration even though it was demonstrated inactive in vitro (see examples).

While not wishing to be bound by any theory, it is believed that the reason these non-classical substituted sulfonamides, which are not active in vitro and have been found effective in vivo, is because the compounds act as either prodrugs, prosuicide inhibitors, or as suicide inhibitors. The terms "prodrug" and "prosuicide inhibitor" mean that they are metabolized to active compound at or prior to the active, in vivo, site.

As will be explained hereinafter, the dosage amounts can vary, and no doubt will vary, but are well within routine experimentation of the treating physician. In the test described hereinafter, the dosage for the topical application has been three drops, with one drop every two minutes. This has been found to be effective, but it is also reasonable to expect that other dosage levels will vary depending upon severity of the case.

It is believed that the present topical application constitutes the first ever topical application for reduction of intraocular pressure by carbonic anhydrase inhibition for glaucoma treatment, of a non-classical type, which is both at a practical dosage and which does not cause side effects at a sufficient magnitude to discourage the patient from continued use.

A certain few of the compounds, per se as described by the generic formula as presented previously, are known. However, none of those have ever been known to have the utility of effective topical treatments for glaucoma. The compounds that the applicants know as previously reported are described in T. H. Maren, *Journal of Pharmacology & Experimental Therapeutics*, 1956, 117, 385.

While the above cited literature does report applicants' preferred non-classical compound, methyl acetazolamide, it is reported only as a diuretic, and there is no suggestion of effective topical use for carbonic anhydrase inhibition.

The reported Maren literature reference shows synthesis of methyl acetazolamide by reacting a mercapto to convert it to a sulfonyl chloride, followed by amination to the N-methyl sulfonamide. In accordance with the present synthesis, unstable intermediates, such as sulfonyl chlorides are avoided, and high yields are obtained. In applicants' process, as detailed in the examples below, a mercapto compound is aminated to provide a N-methyl sulfenamide, which is then oxidized in a non-aqueous oxidation to provide a 75% yield of N-methyl sulfonamide.

The following examples are offered to further illustrate the synthesis of the compound of this invention, the making of topical treatment compositions using the same, and to provide data showing decrease of intraocular pressure in the cornea of rabbits as well as the lack of effectiveness of these non-classical compounds in vitro. They are intended to further illustrate, but not necessarily limit the invention and it is understood that certain modifications and changes, both in technique and composition and structure, may be made, without departing from structure, function and operation of the invention.

EXAMPLE 1

Methyl acetazolamide was prepared in the following manner: 0.5 g of 2-amino-1,3,4-thiadiazole-5-mercaptan was mixed with 0.5 ml of acetic anhydride and a 1 ml of acetic acid to make it slurry. While being stirred, an infra red lamp was used to heat the mixture until it formed a yellowish paste.

Water was added and the product was filtered and washed with water. The product was then taken up in 10% sodium carbonate and reprecipitated with dilute acetic acid while being cooled in an ice bath.

% yield=90%, m.p. 290°-293° C., m.w.=175.232; mass spec m/e=175.

Methyl acetazolamide. 0.15 g of sodium hydroxide was dissolved in water, and a 1 g of 2-acetylamino-1,3,4-thiadiazole-5-mercaptan was dissolved in it. This solution and 15 ml of 5.25% NaOCl (3 equivalents) were simultaneously and slowly added with constant stirring to 35 ml (excess) 40% aqueous methyl amine that had been cooled to $-10°$ C. The reaction mixture temperature was not allowed to rise above 10° C. Dilute acetic acid was used to bring the pH to 7 and cause the sulfenamide to precipitate. The sulfenamide was filtered, allowed to dry somewhat and then dissolved in 1,2-dimethoxyethane (DME). 3 g (2.5 eq) of m-chloroperoxybenzoic acid (m-CPBA) was also dissolved in DME. The sulfenamide solution was cooled to 0° C. and the m-CPBA slowly added. The mixture was allowed to stir for 24 hours. The DME was removed under vacuum and the excess m-CPBA neutralized with a sodium bicarbonate solution. The product was filtered and washed with water.

% yield=75%; m.p. 256°-258° C.; m.w.=236.3; nmr(DMSO) (13, s) (8,m) (2.7, d) (2.3 s).

EXAMPLE 2

The simplified method of Maren (Journal of Pharmacology and Experimental Therapeutics (1960), 130, 389), was used to determine the in vitro carbonic anhydrase activity of methyl acetozolamide and acetazolamide.

The procedure required the use of a specialized glass reaction vessel to which was added 0.4 ml phenol red indicator (0.00125%), 0.25 to 0.30 ml heparinized blood containing 2 enzyme units of carbonic anhydrase, 0.1 ml drug solution (0.01 to 100 mg/L) and 0.1 ml of 0.255M carbonate buffer. One enzyme unit was defined as the amount required to complete the reaction recooled to 0° C. before use. Water was added to the reaction vessel which was kept in a water bath at $0\pm0.25°$ C. The reaction cell was constantly purged with $CO_2$ at a rate of 200 to 250 ml/min. Each reagent was added at a specified time and in a specified order. The time between the addition of the methyl acetazolamide solution and the carbonate buffer (the last ingredient to be added) is the time required for carbonic anhydrase to reach an equilibrium with each drug. This time can vary from ten seconds for sulfanilamide to ten minutes for ethoxzolamide. The time required for the reaction begins with the addition of carbonate buffer and was completed with the indicator changed from red to yellow. A stopwatch was used to determine the reaction time which for a typical catalyzed reaction occurred in about 20 seconds. An uncatalyzed reaction occurred in about 60 seconds. Reaction time was the time for the uncatalyzed reaction time. The reaction times remain constant once equilibrium has been attained. By varying the time before adding the carbonate buffer and then determining the reaction time, the equilibration time can be accurately determined. The reaction time was averaged over three determinations. A range of drug concentrations were reacted and the concentration of drug causing 50% inhibition of enzyme ($I_{50}$) read from a plot of reaction time against drug concentration. (If two enzyme units are added, then the concentration of drug yielding a reaction time corresponding to the activity of one unit is taken as the $I_{50}$). An enzyme unit (e.u.) was calculated from:

$$e.u. = \frac{time_{uncat.} - time_{cat.}}{time_{cat.}}$$

Results: The averaged $I_{50}$ values were 0.00914 and 0.520 mg for acetazolamide and methyl acetazolamide. The significance of these numbers are best interpreted as a ratio (0.52/0.00914) such that the activity of methyl acetazolamide is nearly non-existent or 1/60th of acetazolamide.

EXAMPLE 3

Salted Rabbit Test

For reasons that are not quite fully understood, it has been found that if the rabbits prior to exsanguanation are treated with a salt diet, the test results are more reproducible and accurate. In particular, an initial drop from the test formulation followed by two drops at one minute intervals are applied to one eye of each of six adult white rabbits that had been maintained ona diet containing 0.5% sodium. The treated eye was selected randomly, whereas, the fellow eye received placebo; the observer was masked. Results identified a small but significant reduction of intraocular pressure in the treated eye at 30, 60 and 120 minutes.

In particular, a 1% w/v suspension of methyl acetazolamide was prepared in a standard vehicle consisting of aqueous pH 7.8 phosphate buffer, 0.05% w/v Tween 80, and sufficient NaCl to make the preparation isotonic. One drop, followed by two drops each at one minute intervals, was applied to one eye of normal adult white rabbits. Six rabbits were used in the experiment. The treated eye was selected randomly, whereas, the fellow eye received placebo. The observer was masked.

The intraocular pressure (IOP) was measured with a Digilab Pneumotonometer, initially and every ten minutes for 120 minutes following instillation of the anti-glaucoma agent. A drop of local anesthetic was applied just prior to making the measurement.

50–67% yields and provided satisfactory confirming identification data on elemental, mass spectral, and nuclear magnetic resonance analyses all indicating the presence of the stated compounds. 4-nitro, m.p. 147°–149° C.; 4-chloro, m.p. 81°–83° C.

TABLE I

| | IOP* Changes Through 120 Minutes (Time of Measurement Minutes) | | | | | | | | | | | | |
|---|---|---|---|---|---|---|---|---|---|---|---|---|---|
| | 0 | 10 | 20 | 30 | 40 | 50 | 60 | 70 | 80 | 90 | 100 | 110 | 120 |
| Rabbit No. | | | | | | | | | | | | | |
| 1 | 3 | −4 | −2 | −3 | 0 | −5 | −3 | −4 | −3 | −2 | −4 | −2 | −3 |
| 2 | 2 | −2 | 0 | −2 | −1 | −2 | 1 | −2 | −3 | 1 | 0 | −2 | 0 |
| 3 | 2 | −4 | −4 | −3 | −1 | −2 | −3 | −4 | −4 | −1 | −3 | −2 | −3 |
| 4 | 2 | −2 | −3 | −3 | 0 | −1 | −2 | 0 | −3 | −4 | −4 | 0 | −1 |
| 5 | 0 | 0 | 1 | −2 | 0 | 0 | −2 | 2 | 1 | 0 | −2 | 1 | −1 |
| 6 | 2 | 0 | −2 | −1 | — | −1 | −1 | −2 | 0 | 3 | −3 | 1 | −1 |
| Av. Chg. | 1.83 | −2 | −1.67 | −2.33 | −0.40 | −1.83 | −1.67 | −1.67 | −2.14 | −1.50 | −2.67 | −0.67 | −1.5 |
| Std. Dev. | .98 | 1.79 | 1.86 | 0.82 | 0.55 | 1.72 | 1.51 | 2.34 | 1.86 | 1.87 | 1.51 | 1.06 | 1.22 |
| Paired t val. | — | −4.2 | −3.72 | −7.3 | −4.10 | −4.13 | −4.35 | −3.09 | −4.22 | −3.53 | −3.53 | −3.91 | −4.75 |
| Probability (l.t) | — | .01 | .05 | .001 | .01 | .01 | .01 | .05 | .01 | .05 | .05 | .05 | .01 |

IOP* Changes = $(IOP_{DET} - IOP_{CET}) - (IOP_{DEO} - IOP_{CEO})$ where,
$IOP_{DET}$ = IOP measurement (mm Hg) of dosed eye at time t.
$IOP_{DEO}$ = IOP measurement (mm Hg) of dosed eye at t = 0, but prior to receiving dose.
$IOP_{CET}$ = IOP measurement (mm Hg) of control (non-dosed) eye ate time t.
$IOP_{CEO}$ = IOP measurement (mm Hg) of control eye at time t = 0
*Difference in IOP measurements (mm Hg) between both eyes just prior to dosing at t = 0 (i.e., $IOP_{DEO} - IOP_{CEO}$).
The lowering of IOP was statistically significant at all time intervals.

EXAMPLES 4 AND 5

Synthesis of
1-(N-hydroxy-N-methyl-sulfonamido)-4-substituted benzene.

R=4-nitrophenyl (example 4)
R=4-chlorophenyl (example 5)

N-methylhydroxylamine hydrochloride (0.009 mol) was dissolved in a mixture of methanol (10 ml) and pyridine (0.73 ml) at 0° C. 4-substituted benzenesulfonyl chloride (0.0045 mol) was added in portions over a 15 minute period. The reaction was removed from the ice bath and stirred for 15 hours at room temperature. Water (75 ml) was added and the solution cooled in an ice bath. The precipitated product was collected by vacuum filtration and purified by column chromatography using silica gel (25 g) with 9:1 toluene/ethyl acetate as the eluant. The purified 1-(N-hydroxy-N-methylsulfonamido)-4-substituted benzenes were obtained in

EXAMPLES 6 AND 7

A 1% solution of 1-(N-hydroxy-N-methylsulfonamido)-4-chlorobenzene and a 1% solution of 1-(N-hydroxy-N-methylsulfamido)-4-nitrobenzene were prepared for two separate experiments, examples 6 and 7 respectively. The vehicle consisted of aqueous pH 7.2 phosphate buffer. One drop, followed by two drops each at one minute intervals, was applied to one eye of normal adult white rabbits. Six rabbits were used in example 6 and twelve rabbits in example 7. The treated eye was selected randomly, whereas, the fellow eye received placebo. The observer was masked. The intraocular pressure (IOP) was measured with a Digilab pneumotonometer, initially and every ten minutes for 180 minutes in each experiment following instillation of the anti-glaucoma agent. A drop of local anesthetic was applied to each eye just prior to making the measurement.

TABLE 1

RESULTS - EXAMPLE 6
IOP changes through 180 minutes of
1-(N—hydroxy-N—methylsulfonamido)-4-chlorobenzene

| | Time of Measurement, Minutes | | | | | | | | | |
|---|---|---|---|---|---|---|---|---|---|---|
| | 0 | 20 | 40 | 60 | 80 | 100 | 120 | 140 | 160 | 180 |
| Ave. change = | 0.417 | 0.617 | 1.00 | −1.25 | 0.167 | 0.667 | 0.333 | −.333 | −0.25 | −0.25 |
| Stnd deviation = | 1.16 | 1.19 | 3.62 | 1.71 | 1.75 | 1.44 | 1.44 | 1.67 | 1.22 | 1.54 |
| Paired t-value = | — | −.36 | .51 | 2.67* | −0.39 | 0.446 | −0.15 | −1.22 | −1.134 | −1.14 |

*Probability is less than 0.025 at 60 minutes.

TABLE 2

RESULTS - EXAMPLE 7
IOP changes through 180 minutes of
1-(N—hydroxy-N—methylsulfamido)-4-nitrobenzene

| | Time of Measurement, Minutes | | | | | | | | | | | |
|---|---|---|---|---|---|---|---|---|---|---|---|---|
| | 0 | 10 | 20 | 30 | 40* | 50** | 60* | 70** | 80* | 90 | 100 | 110 | 120 |
| Ave. change = | 0.167 | 0.333 | −0.333 | −.667 | −1.67 | −1.83 | 1.67 | −2.0 | −1.167 | 0.2 | −0.5 | −0.33 | −1.00 |
| Stnd deviation = | 0.983 | 0.817 | 2.25 | 2.25 | 1.63 | 0.983 | 1.21 | 1.67 | 0.752 | 1.095 | 1.64 | 1.506 | 1.264 |
| Paired t values = | — | 0.875 | −0.152 | −0.455 | −1.76 | −2.68 | −2.15 | −2.11 | −1.81 | 0.558 | −0.389 | −0.207 | −1.162 |

*Probability is less than 0.05 at 40 and 80 minutes
**Probability is less than 0.025 at 50, 60 and 70 minutes.

What is claimed is:

1. A topical composition for eye drop treatment of glaucoma, comprising:

a small but intraocular eye pressure reducing effective amount of a non-classical carbonic anhydrase inhibitor of the formula:

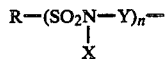

wherein

R is selected from the group consisting of phenyl and 4-substituted phenyl wherein the substituent is selected from the group consisting of chloro, nitro, fluoro, hydroxy, hydroxyethoxy, methoxy and ethoxy; and X is selected from the group consisting of hydrogen and hydroxyl; and Y is selected from the group consisting of $C_1$ to $C_6$ alkyl and hydrogen, and if either X or Y is hydrogen, the other is not hydrogen; and n is either 1 or 2; and from about 0.01% by weight to about 0.10% by weight of a wetting agent, from about 0.004% by weight to about 0.02% by weight of an anti-bacterial agent; and an isotonic inert, non-irritating and nontoxic topical ophthalmic carrier having a pH within the range of about 4.0 to about 8.0.

2. The composition of claim 1 wherein said sulfonamide analogue is at a concentration of from about 0.25% to about 5% by weight of said eye drop composition.

3. The composition of claim 2 wherein said sulfonamide derivative is from about 0.5% to about 2.0% by weight of said eye drop composition.

4. The composition of claim 3 wherein said sulfonamide derivative is about 1% by weight of said eye drop composition.

5. The composition of claim 1 wherein said composition is buffered to a pH of from about 6.8 to about 7.8.

6. The composition of claim 1 wherein said wetting agent is Tween 80.

7. The composition of claim 1 wherein said anti-bacterial agent is benzalkonium chloride.

8. The composition of claim 1 wherein X is hydrogen; Y is methyl and n is one.

* * * * *